US008647621B2

(12) United States Patent
Lees

(10) Patent No.: US 8,647,621 B2
(45) Date of Patent: Feb. 11, 2014

(54) METHOD OF PRODUCING PROTEIN-CARBOHYDRATE VACCINES REDUCED IN FREE CARBOHYDRATE

(75) Inventor: Andrew Lees, Silver Spring, MD (US)

(73) Assignee: Fina BioSolutions, LLC, Rockville, MD (US)

( * ) Notice: Subject to any disclaimer, the term of this patent is extended or adjusted under 35 U.S.C. 154(b) by 10 days.

(21) Appl. No.: 13/387,326

(22) PCT Filed: Jul. 27, 2010

(86) PCT No.: PCT/US2010/043387
§ 371 (c)(1),
(2), (4) Date: Feb. 19, 2012

(87) PCT Pub. No.: WO2011/017101
PCT Pub. Date: Feb. 10, 2011

(65) Prior Publication Data
US 2012/0135030 A1    May 31, 2012

Related U.S. Application Data

(60) Provisional application No. 61/228,784, filed on Jul. 27, 2009.

(51) Int. Cl.
*A61K 35/00*    (2006.01)
(52) U.S. Cl.
USPC .......................................................... 424/124
(58) Field of Classification Search
None
See application file for complete search history.

(56) References Cited

U.S. PATENT DOCUMENTS

| | | | |
|---|---|---|---|
| 4,160,861 A * | 7/1979 | Cole et al. .................. 536/7.1 |
| 4,356,170 A | 10/1982 | Jennings et al. | |
| 4,540,573 A | 9/1985 | Neurath et al. | |
| 4,663,160 A | 5/1987 | Tsay et al. | |
| 4,678,553 A | 7/1987 | Mandie et al. | |
| 4,695,624 A | 9/1987 | Marburg et al. | |
| 5,039,607 A | 8/1991 | Skold et al. | |
| 5,306,492 A | 4/1994 | Porro | |
| 5,360,897 A | 11/1994 | Anderson | |
| 5,425,946 A | 6/1995 | Tai et al. | |
| 5,585,100 A | 12/1996 | Mond et al. | |
| 5,651,971 A | 7/1997 | Lees | |
| 5,681,570 A | 10/1997 | Yang et al. | |
| 5,693,326 A | 12/1997 | Lees | |
| 5,747,663 A | 5/1998 | Colpan et al. | |
| 5,849,301 A | 12/1998 | Lees | |
| 5,955,079 A | 9/1999 | Mond et al. | |
| 6,087,328 A | 7/2000 | Lees | |
| 6,146,902 A | 11/2000 | McMaster | |
| 6,248,334 B1 | 6/2001 | Lees et al. | |
| 6,284,250 B1 | 9/2001 | Lees et al. | |
| 6,299,881 B1 | 10/2001 | Lees et al. | |
| 6,309,646 B1 | 10/2001 | Lees | |
| 6,428,703 B1 | 8/2002 | Zinn et al. | |
| 6,432,679 B1 | 8/2002 | Mond et al. | |
| 6,585,973 B1 | 7/2003 | Lees | |
| 6,596,172 B1 | 7/2003 | Kopf | |
| 6,756,041 B2 | 6/2004 | Lees et al. | |
| 6,765,091 B1 | 7/2004 | Bencomo et al. | |
| 7,094,883 B1 | 8/2006 | Cassels et al. | |
| 7,101,562 B1 | 9/2006 | Lees et al. | |
| 7,166,708 B2 | 1/2007 | Lees et al. | |
| 7,250,494 B2 | 7/2007 | Stinson et al. | |
| 7,452,533 B2 | 11/2008 | Walsh et al. | |
| 7,470,441 B2 | 12/2008 | Van Der Giessen et al. | |
| 7,566,540 B2 | 7/2009 | Cassels et al. | |
| 7,777,017 B2 | 8/2010 | Stinson et al. | |
| 2002/0054879 A1 | 5/2002 | Lees et al. | |
| 2002/0119529 A1 | 8/2002 | Mond et al. | |
| 2003/0082211 A1 * | 5/2003 | Gorringe et al. ........... 424/234.1 |
| 2003/0215436 A1 | 11/2003 | Walsh et al. | |
| 2003/0224000 A1 | 12/2003 | Kokai-Kun et al. | |
| 2003/0235578 A1 | 12/2003 | Stinson et al. | |
| 2004/0052779 A1 | 3/2004 | Stinson et al. | |
| 2005/0074460 A1 | 4/2005 | Lees et al. | |
| 2005/0075486 A1 | 4/2005 | Cassels et al. | |
| 2005/0169941 A1 | 8/2005 | Lees | |
| 2005/0222434 A1 | 10/2005 | Bessodes et al. | |
| 2006/0165822 A1 | 7/2006 | Van Der Giessen et al. | |
| 2007/0065465 A1 | 3/2007 | Lees et al. | |
| 2007/0292404 A1 | 12/2007 | Walsh et al. | |
| 2008/0019976 A1 | 1/2008 | Stinson et al. | |
| 2009/0081180 A1 | 3/2009 | Walsh et al. | |
| 2011/0263834 A1 | 10/2011 | Lees et al. | |

FOREIGN PATENT DOCUMENTS

| | | |
|---|---|---|
| EP | 1163000 | 2/2008 |
| JP | 2004-501869 | 1/2004 |
| JP | 08-510210 | 4/2008 |
| WO | WO9521177 | 8/1995 |
| WO | WO9521179 | 8/1995 |

(Continued)

OTHER PUBLICATIONS

PCT Search Report for PCT/US2010/055107, dated Jul. 28, 2011.

(Continued)

*Primary Examiner* — Albert Navarro
(74) *Attorney, Agent, or Firm* — Remenick PLLC

(57) ABSTRACT

This invention is directed to processes for reducing the level of free carbohydrate from a solution of protein-linked carbohydrate (conjugate) and non-linked carbohydrate. In this process, the conjugate is adsorbed to a hydrophobic membrane while the carbohydrate is not. The conjugate is then desorbed from the membrane, yielding a solution that is substantially reduced in free carbohydrate.

19 Claims, 8 Drawing Sheets

(56) References Cited

FOREIGN PATENT DOCUMENTS

| | | |
|---|---|---|
| WO | WO96/17941 | 6/1996 |
| WO | WO96/40662 | 12/1996 |
| WO | WO01/70685 | 9/2001 |
| WO | WO01/78787 | 10/2001 |
| WO | WO03/057849 | 7/2003 |
| WO | WO03/097699 | 11/2003 |
| WO | WO2004104811 | 12/2004 |
| WO | WO2005/056608 | 6/2005 |
| WO | WO2006-032475 | 3/2006 |
| WO | WO 2008-021076 | 2/2008 |

OTHER PUBLICATIONS

PCT Patentability Report for PCT/US2010/055107, dated Jul. 28, 2011.
R. Wong & H, Tse, Lateral Flow Immunoassay, Humana Press (2009).
Bioconjugate Protocols: Strategies and Methods (Methods in Moldecular Biology) Christof M. Niemeyer (Editor) Humana Press (2009).
PCT Patentability for PCT/US2010/055107, dated May 8, 2012.
D. C. Watson, J. B. Robbins, and S. C. Szu, "Protection of mice against Salmonella typhimurium with an O-specific polysaccharide-protein conjugate vaccine," Infection and Immunity 60:4679-4686, 1992.
E. Konadits, J. Shiloach, D. A. Bryla, J. B. Robbins, and S. C. Szu, "Synthesis, characterization, and immunological properties in mice of conjugates composed of detoxified lipopolysaccharide of Salmonella paratyphi A bound to tetanus toxoid, with emphasis on the role of O-acetyls," Infect Immun. Jul. 1996; 64(7):2709-15.
Sehneerson R, Barrera O, Sutton A, Robbins JB. Preparation, characterization, and immonogenicity Haemophilus influenzae type b polysaccharide-protein conjugates. J Exp Med. Aug. 1, 1980;152(2):361-376.
Search Report for PCT/U52010/043387, dated Apr. 27, 2011.
Chinese Office Action of Chinese application No. 200580010225.4, dated May 18, 2012.
PCT Search Report for PCT/US10/61313, dated Feb. 15, 2011.
PCT Patentability Report for PCT/US10/61313, dated Feb. 15, 2011.
Chu, et al., "Further studies on the immunogenicity of Haemophilus influenzae type b and pneumococcal type 6A polysaccharide-protein conjugates," Inf. & Imm., 40:245-256 (1983).
Jennings, et al., "Conjugation of meningococcal lipopolysaccharide R-type oligosaccharides to tetanus toxoid as a route to a potential vaccine against group B Neisseria meningitides," Inf. & Immun., 43:407-412 (1984).
Laferriere et al., "The Synthesis of Streptococcus pnemoniae polysaccharide-tetanus toxoid conjugates and the effect of chain length on immunogenicity," Vaccine, 15:179 (1997).
Kohler, et al., "Continuous cultures of fused cells secreting antibody of predefined specificity," Nature, 256:495-7 (1975).
Morath, et al., "Structure-function relationship of cytokine induction by lipoteichoic acid from Staphylococcus aureus," J. Exp. Med. 193(3), p. 393-397 (2001).
PCT Search Report for PCT/US05/003040, dated Mar. 8, 2006.
Marcaurelle, L., et al., "Synthesis of oxime-linked mucin mimics containing tumor-related Tn and sialyl Tn antigens," Organic Letters, vol. 3, No. 23, p. 3691-3694 (2001).
Webb, R.R., et al., "Synthesis of 1-(aminooxy)-4-A(3-nitro-2-pyridyl) dithiou butane and 1-(aminooxy)-4-A(3-nitro-2-pyridyl) dithiou but-2-ene, novel heterobifunctional cross-linking reagents," Bioconjugate Chemistry, ACS, Washingtion, DC, US, vol. 2, No. 2, p. 96-99 (1990).
Brask, J. et al., "Carbopetptides: chemoselective ligation of peptide aldhehydes to an aminooxy-functionalized D-galactose template," Journal of Peptide Science, vol. p. 290-999 (2000).
Zeng, W. et al., "Assembly of synthetic peptide vaccines by chemoselective ligation of epitopes: influence of different chemical linkages an epitode orientations on biological activity," Vaccine, Butterworth Scientific, Guildford, GB, vol. 19, No. 28-29, p. 3843-3852 (Jul. 16, 2011).
Kubler-Kielb, J., et al., "A new method for conjugation of carbohydrates to proteins uing an aminooxy-thiol heterobifunctional linker," J. Org. Chem., vol. 70, p. 6987-6990 (Jul. 2005).
PCT Patentability Report for PCT/US05/003040, dated Jul. 29, 2006.
EPO Exam Report for PCT/US05/003040, dated Feb. 22, 2008.
EPO Exam Report for PCT/US05/003040, dated Jul. 11, 2007.
AU Exam Report for PCT/US05/003040, dated Mar. 4, 2011.
JP Exam Report for PCT/US05/003040, dated May 19, 2011.
Renaudet & Dumy, "Chemoselectively template-assembled glycopeptides presenting clustered cancer related t-antigen," Tetrahedron Letters, vol. 45, No. 1, p. 65-68 (Jan. 2004).
JP Exam Report for PCT/US05/003040, dated Nov. 22, 2010.
Chinese Exam Report for PCT/US05/003040, dated Oct. 24, 2011.
Chinese Exam Report for PCT/US05/003040, dated Apr. 3, 2009.
CA Exam Report for PCT/US05/003040, dated Jun. 11, 2010.
CA Exam Report for PCT/US05/003040, dated Jul. 13, 2010.
AU Exam Report for PCT/US05/003040, dated Sep. 14, 2007.
India Exam Report for PCT/US05/003040, dated Sep. 14, 2007.
PCT Patentability Report for PCT/US2010/061133, dated Jun. 19, 2012.
ARKIVOC, 2007(iii), pp. 5-12.
"2-Cyanopyridazin-3(2H)-ones: effective and chemoselective electrophilic cyanating agents," Kim, et al., Tetrahedron, vol. 61, Jun. 2005, pp. 5889-5894.
PCT Patentability Report for PCT/US2010/043387, dated Apr. 27, 2011.
Webb, R.R., et al., "Synthesis of 1-(aminooxy)-4-A(3-nitro-2-pyridyl) dithiou butane and 1-(aminooxy)-4-A(3-nitro-2-pyridyl) dithiou but-2-ene, novel heterobifunctional cross-linking reagents," Bioconjugate Chemistry, ACS, Washington, DC, US, vol. 1, No. 2, p. 96-99 (1990).
Brask, J. et al., "Carbopetptides: chemoselective ligation of peptide aldhehydes to an aminooxy-functionalized D-galactose template," Journal of Peptide Science, vol. 6 p. 290-299 (2000).
Zeng, W. et al., "Assembly of synthetic peptide vaccines by chemoselective ligation of epitopes: influence of different chemical linkages and epitope orientiatons on biological activity," Vaccine, Butterworth Scientific, Guildford, GB, vol. 19, No. 28-29, p. 3843-3852 (Jul. 16, 2011).
Kubler-Kielb, J., et al., "A new method for conjugation of carbohydrates to proteins uing an aminooxy-thiol heterobifunctional linker," J. Org. Chem., vol. 70, p.6987-6990 (Jul. 2005).

\* cited by examiner

METHOD OF PRODUCING PROTEIN-CARBOHYDRATE VACCINES REDUCED IN FREE CARBOHYDRATE

REFERENCE TO RELATED APPLICATIONS

This application claims priority to U.S. Provisional Application No. 61/228,784 entitled "Method for Producing Protein-Carbohydrate Vaccines Reduced in Free Carbohydrate" filed Jul. 27, 2009, the entirety of which is hereby incorporated by reference.

BACKGROUND

1. Field of the Invention

This invention is directed to a process for reducing the level of free carbohydrate from a solution of protein-linked carbohydrate (conjugate) and non-linked carbohydrate. In addition, the invention is directed to compositions of the process and to vaccines produced.

2. Description of the Background

Vaccines of protein covalently linked to carbohydrate have proven remarkably successful in inducing an immune response to the carbohydrate moiety. Examples of such vaccines, known as "conjugates" are available for *Haemophilus influenzae* type b (e.g., ActHib, Hiberix), *Neisseria meningiditis* types A C W and Y (e.g., Menactra) and *S. pneumoniae* (e.g., Prevnar, Synflorix) For these vaccines to be effective, it is usually necessary to minimize the amount of non-linked carbohydrate present. The term "carbohydrate" is intended to include polysaccharides, oligosaccharides and other carbohydrate polymers, including monomeric sugars.

Specifications for conjugate vaccines set maximum amounts of free polysaccharide that can be present. In contrast, there is generally no specification for the amount of un conjugated protein. In fact, combination vaccines contain significant amounts of unconjugated protein. For example the five-valent vaccine Pentacel, made by Sanofi-Pasteur, contains Hib PRP polysaccharide conjugated to tetanus toxoid (ActHib) as well as free tetanus toxoid. In any case, removal of the unconjugated protein can usually easily be achieved using size exclusion chromatography, tangential flow filtration or the solid phase method described by U.S. Pat. No. 6,284,250. Thus, it is the reduction in the level of the unconjugated carbohydrate that is critical. This reduction can be difficult to achieve with good efficiency and yield. The absence of a good method for removing the unconjugated polysaccharide reduces the yield, increases the needed effort and increases the cost of manufacturing conjugate vaccines.

Conjugate vaccines tend to be of high molecular weight. First because the carbohydrate component itself may be large, secondly because combining the protein and carbohydrate increases the size, and thirdly because there may be additional cross-linking between the components that further increases the molecular weight.

Chromatography is a common means of purifying biological substances. One means of separating the conjugate from free polysaccharide is size exclusion chromatography (SEC), which separates molecules on the basis of their size, or more precisely, their hydrodynamic radius. SEC is a diffusion-limited, non-adsorptive form of chromatography and suffers from low resolution and capacity. Furthermore, SEC is only successful if there is a significant difference in size molecular weight between the conjugate and the free polysaccharide. Because each is polydisperse, there can be significant overlap in their elution profiles and thus resolution is poor. To obtain material with substantially reduced amounts of free polysaccharide, it is generally necessary to discard part of the conjugate, reducing yields. One solution is to use sized, lower molecular weight polysaccharides and then to crosslink the conjugate sufficiently so that the molecular weight increases enough that it can be separated from the sized PS. This process requires extra processing and additional losses of material.

Chromatography resins (e.g. sorbents, media) consist of porous particles that may be functionalized with charges, ligands and other binding partners. In adsorptive chromatography, substances are bound to the sorbent via these groups. However, to be adsorbed, substances need to enter the pores, a process which is diffusion limited. Most of the surface area of the particles is on the porous interior and large molecules, like conjugates diffuse slowly and due to their size, cannot easily access the pores. These difficulties are further accentuated by the fact that conjugates are poly disperse in size. Thus, some of the smaller conjugate may be able to enter the pores and will chromatograph (i.e., separate) differently than conjugate that does not enter the pores. Due to the fact that the conjugates can generally only access the surface of the particles, their binding capacity for conjugates is severely restricted.

A solution is to use oligosaccharides of a size so that the conjugate formed is still of low enough MW that chromatographic separation can be achieved (e.g., ion exchange). Again, this entails additional processing and losses of material.

The conjugate consists of protein linked to carbohydrate, typically in approximately equal mass. Thus, the conjugate takes on many of the physical properties of the carbohydrate moiety. For example, if the carbohydrate is negatively charged, the conjugate will similarly be negatively charged. This creates a further challenge in removing the free carbohydrate as it makes the chemical properties of the conjugate similar to the free carbohydrate. It is therefore preferable to achieve purification by using properties that are unique to the protein component. Such properties could include an ability to bind to immobilized metal affinity chromatography (IMAC) sorbents. IMAC sorbents can interact with protein histidines, tryptophans and cysteines. However, the metal may leach and need to be subsequently removed. This would be undesirable in the manufacture of vaccines. Another property likely to be unique to the protein is hydrophobicity as carbohydrates are usually much less hydrophobic than proteins. Thus, hydrophobic interaction chromatography (HIC) should be useful for separating conjugate from free polysaccharide. In HIC, a lyotropic salt, such as ammonium sulfate, is added. This salt drives binding of the protein to the hydrophobic surface. Hydrophilic substances, like most carbohydrates, may not bind at all and will be found in the flow through volume. Elution is effected by decreasing the concentration of the lyotropic salt or, less frequently, adding modifiers such as detergents, hydrophobic displacers or organic solvents. More hydrophilic material will elute before more hydrophobic molecules. The principles and practice of HIC is described, for example, in Chapter 7 of Protein Purification $2^{nd}$ ed., Janson & Ryden (editors), 1998. Conventional HIC chromatography media suffers from poor capacity and poor recovery for use in purifying conjugate vaccines. It is likely that the bulk of the conjugate is unable to enter the pores.

Other methods for separating the conjugate from the free polysaccharide include tangential flow filtration (TFF). In this process, the solution is rapidly passed across a porous membrane with pores of a nominal molecular weight cutoff lower than that of the conjugate and higher than that of the free carbohydrate. The conjugate is retained and the free polysaccharide passes through into the filtrate. This process can be effective if there is a large difference in molecular weight between the conjugate and the free carbohydrate. If they are too close in size, depending on the molecular weight cutoff of the membrane pores, either too much free carbohydrate is retained or too much of the conjugate is found in the filtrate. Furthermore, it has been found that in some cases, even when there is a large difference in size, poor separation and/or recovery is observed. McMasters (U.S. Pat. No. 6,146, 902) has claimed that the addition of ammonium sulfate can promote separation by TFF. However, this process was unable to be replicated.

Another nonchromatographic method of separation which takes advantage of the difference in hydrophobicity between the protein and the carbohydrate is the selective precipitation of the protein component with a lyotropic salt such as ammonium sulfate (http://en.wikipedia.org1wiki1Ammonium_sulfate-precipitation). As the protein, whether free or conjugated, is more hydrophobic than the polysaccharide it should precipitate at lower salt concentrations than the free carbohydrate. Thus, the conjugate should precipitate while leaving the carbohydrate in solution. The precipitate is separated by centrifugation and then resuspended. In practice, however, some of the free carbohydrate can become entrapped in the precipitate. Furthermore, there can be significant losses associated with the process.

Thus, there is a significant need for an efficient method to remove the unconjugated carbohydrate from the conjugated carbohydrate in conjugate vaccines.

SUMMARY

The present invention overcomes the problems and disadvantages associated with current strategies and designs and provides new tools and methods for reducing the level of free carbohydrate from a solution of protein-linked carbohydrate (conjugate) and non-linked carbohydrate.

One embodiment of the invention is directed to methods for the reduction of free carbohydrates in vaccine preparations. Preferably, the method involves mixing of conjugate and free polysaccharide combined with a sufficient amount of a composition such as, preferably, lyotropic salt such as ammonium sulfate, to promote binding of the conjugate to the hydrophobic membrane. The mixture is passed through a hydrophobic membrane (e.g. HIC membrane) wherein the conjugate (as well as free protein) is adsorbed to the membrane while the hydrophilic carbohydrate flows through. The conjugate is eluted by reducing the concentration of the lyotropic salt as a step or continuous gradient. Preferably the eluent further includes an additive which may be an organic solvent, a detergent, or both, or the additive may be ethylene glycol. It is also preferable to use several steps so that further purification can be achieved, for example to remove other species, such as unconjugated protein. The eluted material is a conjugate with substantially reduced levels of free carbohydrate and may be useful as a vaccine.

Another embodiment of the invention is directed to conjugated carbohydrate compositions such as vaccines that contain substantially reduced or little to no free carbohydrate. Preferable, such compositions are prepared according to the methods of the invention and are vaccines.

Other embodiments and advantages of the invention are set forth in part in the description, which follows, and in part, may be obvious from this description, or may be learned from the practice of the invention.

DESCRIPTION OF THE INVENTION

Figure 1:
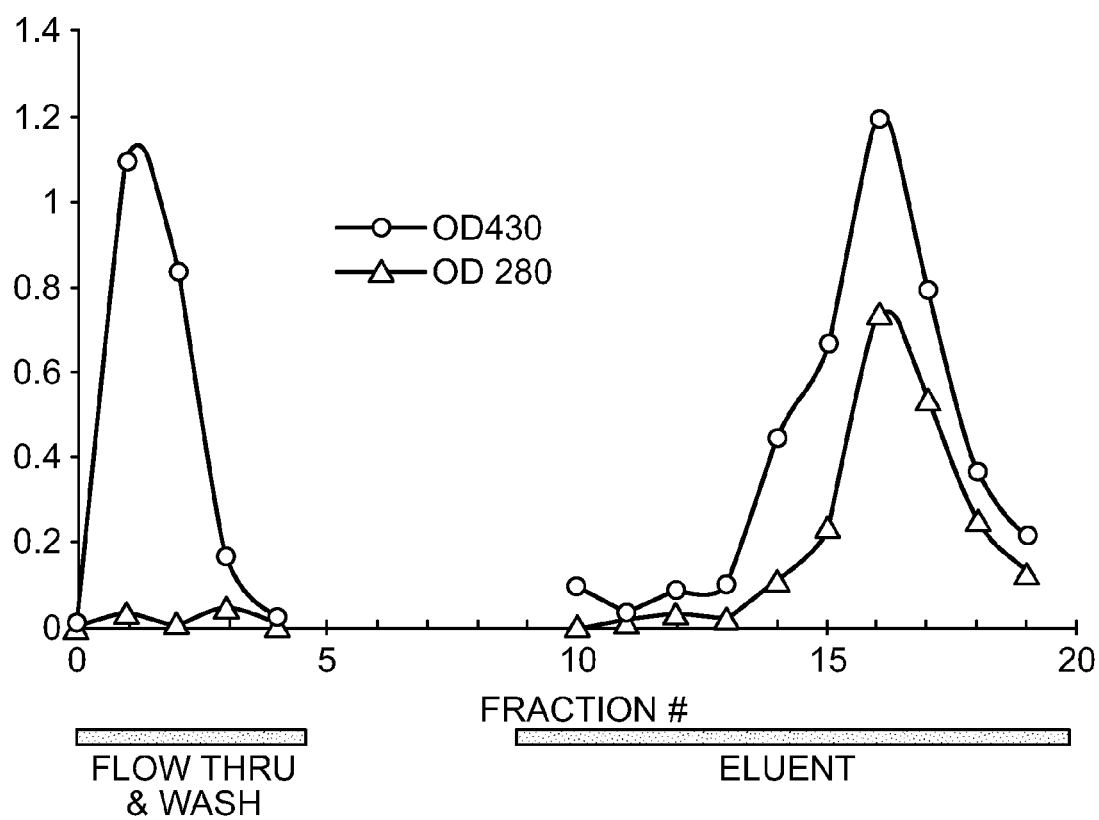
FIG. 1 Fractionation of crude Hib conjugate in HIC membrane indicating the free carbohydrate (as determined by an assay yielding absorbance at 430 nm) and the protein (indicated by absorbance at 280 nm) found in both the unbound fraction and the eluent. For this example, a continuous gradient from 2 to 0 M ammonium sulfate was 15 used for the elution.

Vaccines of protein covalently linked to carbohydrate are prevalent and highly useful in inducing an immune response to a carbohydrate moiety. To maximize and sometimes even allow for their effectiveness, the amount of non~linked carbohydrate in the composition needs to be reduced and often substantially. An effective method for removing the unconjugated polysaccharide from the conjugated polysaccharide has been surprisingly discovered that is both efficient and effective. This method is applicable to both poly- and oligosaccharide conjugates. There is no dependence on the chemistry used to link the protein and carbohydrate nor is the process dependent on the particular carrier protein used. The method is rapid and very simple and gives good recovery of the conjugate. Of particular importance is that the method can be used on high MW polysaccharides that do not separate well by size exclusion chromatography and which do not purify on standard chromatography resins As discussed herein, porous chromatography suffers from many limitations. An alternative form of chromatography uses membranes containing channels to which ligands have been attached. Since the ligands are on the channels and not within pores. the process is convection limited and not diffusion limited. Thus, very high flow rates can be used and even large molecules can access the ligands. Ion exchange membranes have been used for water and buffer purification, DNA and virus purification and "polishing" of protein solutions (removal of residual contaminants).

Membrane chromatography is discussed, for example, in Thommes & Kula Biotech. Prog. 11:357, 1995. While in principle these ion exchange membranes could be used to purify conjugates, a useful separation of the conjugate from the free polysaccharide has yet to be achieved. This is believed to be due to the high level of carbohydrate on the conjugate so that the conjugate has a similar charge as the free carbohydrate.

It has been surprisingly discovered that HIC membranes, in contrast to porous chromatography media, are surprisingly effective at reducing the level of free carbohydrate in conjugate vaccines. In this process, the mixture of the conjugate and free polysaccharide is combined with a sufficient amount of a lyotropic salt such as ammonium sulfate or sodium chloride (or any of the conventional salts) to promote binding of the conjugate to the hydrophobic membrane. The mixture is then passed through the hydrophobic membrane. A preferred membrane is Sartobind nano Phenyl membrane (3 ml) (commercially available from Sartorious AG). The conjugate (as well as free protein) is adsorbed to the membrane while the hydrophilic carbohydrate flows through. The conjugate is eluted by reducing the concentration of the lyotropic salt. A step gradient or continuous gradient can be employed. In some cases, it is preferable to use several gradient steps so that further purification can be achieved, for example to remove other species, such as unconjugated protein. The eluted material is conjugate with substantially reduced levels of free carbohydrate.

Other forms of chromatography that use channels and not pores are also preferred. Examples of such forms of chromatography include so-called monolith matrices or columns. These are columns are cast as a single unit, instead of consisting of small particles. Such monolith columns are available, for example, from BIA Separations (Europa Strasse 8 9524 Villach, Austria). Phenyl monoliths can be prepared in the same way as phenyl membranes are made (Deraz et al. Enz & Microb Tech, 40:786, 2007).

Preferably the method results in a free-carbohydrate reduction of 40% or greater, 50% or greater, 60% or greater, 70% or greater, 75% or greater, 80% or greater, or 85% or greater. More preferably the reduction is 90% or greater or 95% or greater, more preferably a reduction of 98% or greater or of 99% or greater, and more preferably a reduction of as near 100% as is detectable.

The examples shown here are for Hib PRP tetanus conjugate vaccine. Other examples of conjugate vaccines are Hib PRP conjugated to CRM197 or diphtheria toxoid, conjugates of *Neisseria meningitis* capsular polysaccharide, conjugates with *S. pneumoniae* capsular polysaccharides to CRM197, tetanus toxoid or protein D. Thus, the method is not limited by the carrier protein, the carbohydrate, the molecular weight of the carbohydrate or the chemistry used to link the protein and the carbohydrate.

The following examples illustrate embodiments of the invention, but should not be viewed as limiting the scope of the invention.

EXAMPLES

Purification of Bib Conjugate Using HIC Membranes

Hib PRP is the capsular polysaccharide of *Haemophilus influenzae* type b. Hib PRP was linked to tetanus toxoid (TT) as generally described by Schneerson et al. Infect Immun, 152:361, 1980. This material was prepared at the Serum Institute of India (Pune, India) as an unpurified mixture, containing both conjugated and unconjugated PRP. This is referred as crude Hib conjugate.

15 ml Hib conjugate, containing both Tr-Hib PRP conjugate and unconjugated Hib PRP was made 2 M ammonium sulfate and adjusted to pH 6. The final volume was about 17 ml. A Sartorius HIC phenyl membrane unit (3 ml) qA equilibrated with 50 mM sodium phosphate buffer+2 M ammonium sulfate, pH 6. 6 ml of the conjugate in AS buffer was pumped through the device, followed by the equilibration buffer (~35 ml total) with fractions of approximately 8 ml collected. A gradient from 2 M ammonium sulfate to 0 M was run with fractions of 2 ml collected. Fractions were assayed for carbohydrate using the resorcinol sulfuric acid method (Monsigny et al. Anal Biochem (175:525, 1988) and for protein by absorbance at 280 urn. As shown, the carbohydrate is found in both the unbound fraction and the eluent, while the protein is found mainly in the gradient elution fractions, coincident with the eluting carbohydrate (FIG. 1). Thus, the unconjugated carbohydrate is separated from the conjugated carbohydrate, resulting in a conjugate with substantially reduced levels of free carbohydrate.

Figure 2:
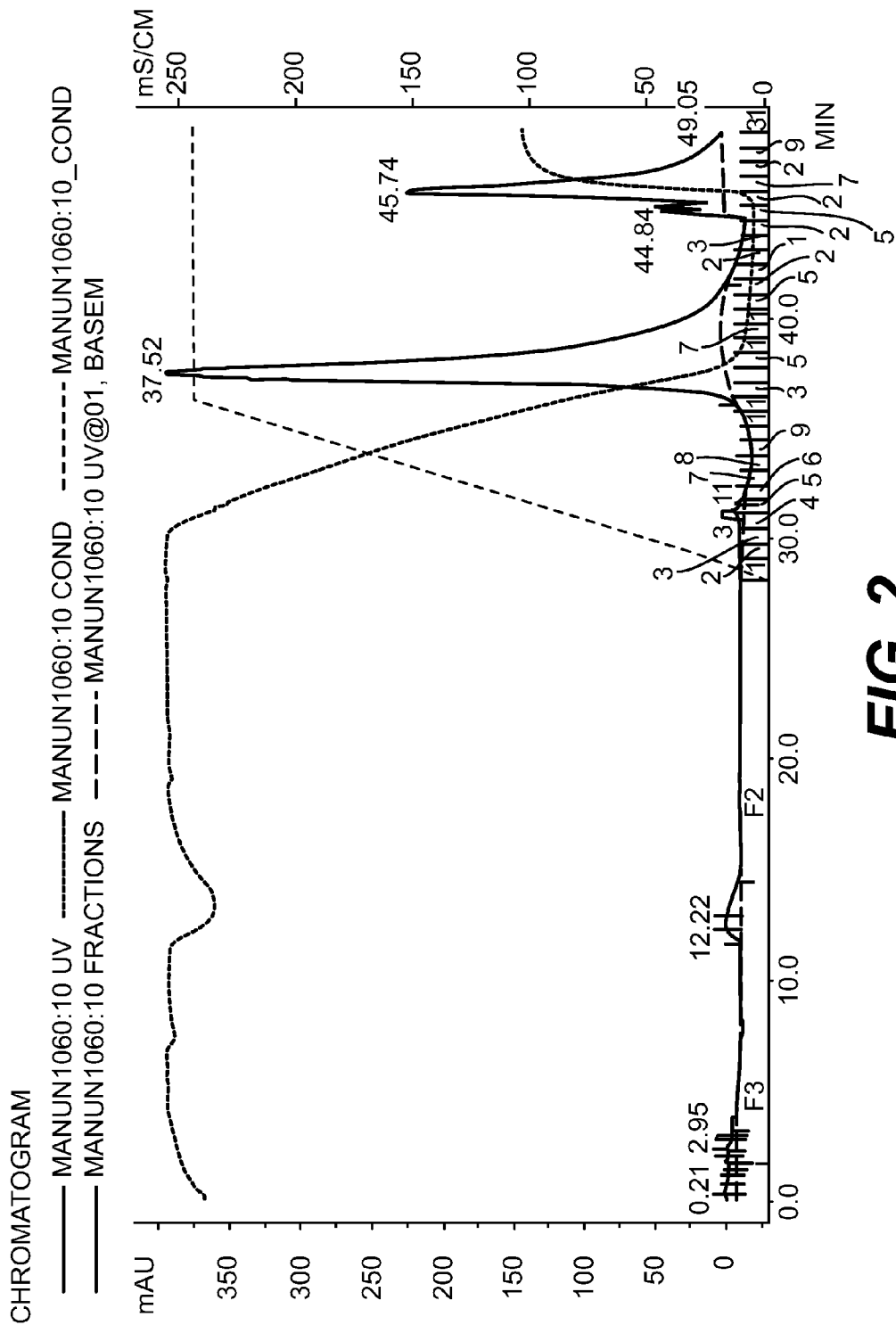
FIG. 2. An absorbance trace at 280 nm. For this example, binding was performed at 2.5 M ammonium sulfate and a step gradient from 2.5 M to 0 M ammonium sulfate was used for elution.

The experiment was repeated, but using an equilibration buffer containing 2.5 M ammonium sulfate. The crude Hib PRP conjugate was made 2.5 M ammonium sulfate prior to pumping it through the membrane at 2 ml/min. The membrane was washed at 2 ml/min with the equilibration buffer and then eluted with a 20 ml gradient to 0 M ammonium sulfate at a flow rate of 3 ml/min. FIG. 2 indicates the absorbance trace at 280 nm. It is seen that very little absorbance is found in the unbound fractions and washes, whereas a large peak, corresponding to the protein, was desorbed at low salt. The membrane was then washed with 0.5 M NaOH and a smaller peak with absorbance at 280 nm emerged. This illustrates that the protein component is retained on the membrane.

Figure 3:
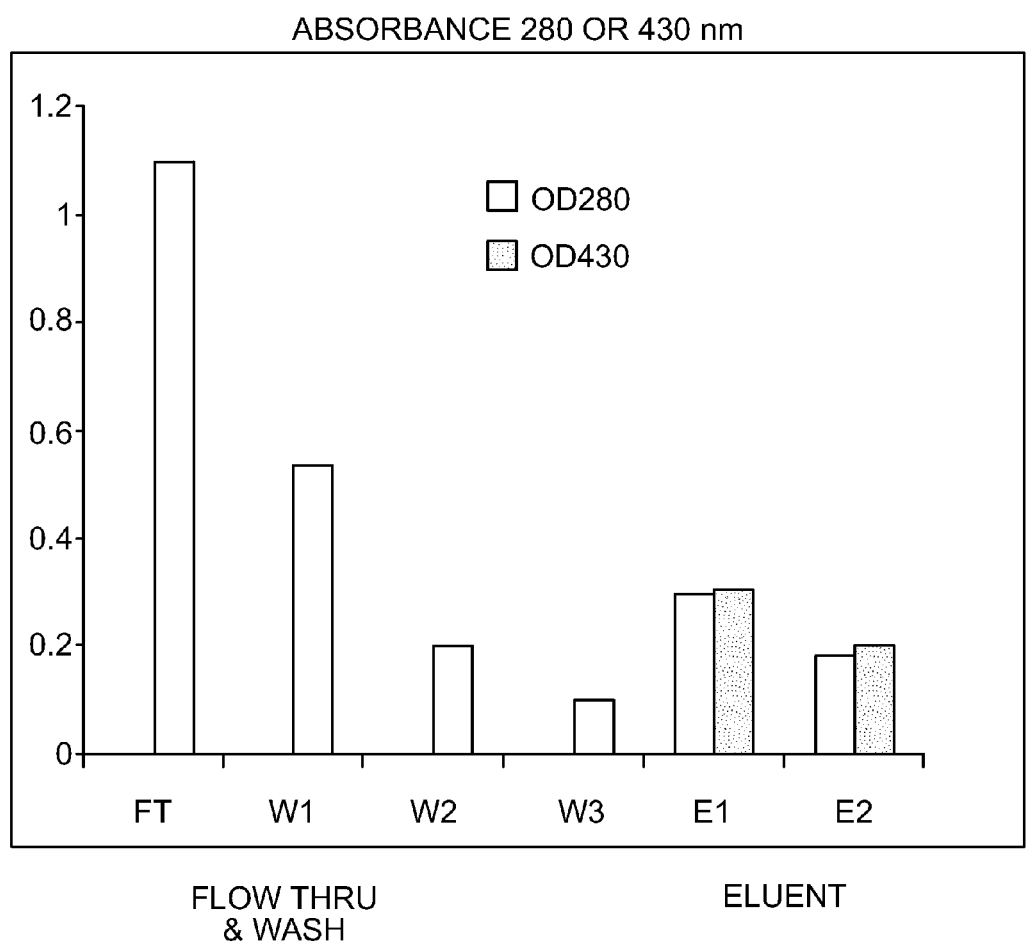
FIG. 3. Fractions obtained were assayed for carbohydrate using the resorcinol assay and for protein by absorbance at 280 run showing that the carbohydrate was found in both the flow through and the elution fractions, but that detectable protein was found only in the elution fractions.
Figure 4:
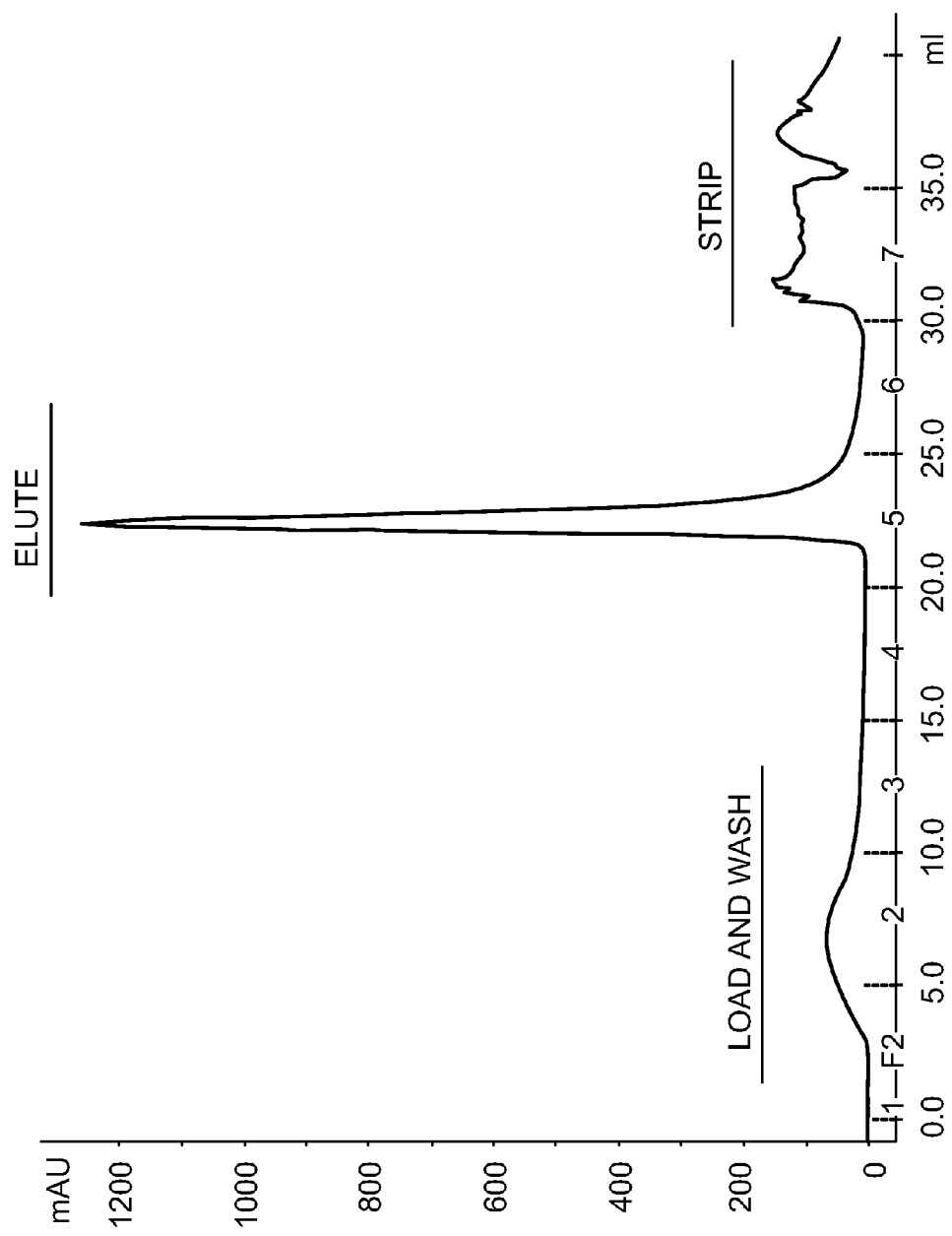
FIG. 4. Chromatogram of Hib conjugate eluted from HIC membrane with additives.

Step gradient elution. The membrane device was equilibrated with 50 mM 15 ME~+2.5 M ammonium sulfate, pH 6 and 6 ml of the crude Hib conjugate in the same buffer was pumped onto the membrane. Flow through and several wash fractions were collected (~10 mls each) and the conjugate was eluted with 50 mM MES, pH 6, without ammonium sulfate. Two 6 ml fractions were collected. Each fraction was assayed for carbohydrate using the resorcinol assay and for protein by absorbance at 280 nm (FIG. 3). It is seen that the carbohydrate is found in both the flow through and the elution fractions but the protein is found mainly in the elution fractions. Thus, the conjugate is substantially reduced in free polysaccharide.

Use of Additives to Elute Conjugate from the HIC Membrane.

A variety of additives, such as organic solvents or detergents are often used to promote desorbtion in hydrophobic interaction chromatography. This example shows the use of ethylene glycol.

Hib-TT Sample Preparation and Modifications.

Crude Hib conjugate was prepared to a final protein concentration corresponding to an $A_{280nm}$ value of 1.0 and filtered through a 0.2 μm syringe filter. The HIC membrane was equilibrated with 5 column volumes (CVs) of 50 mM potassium phosphate buffer, pH 7.0-7.2, containing 1.0 M ammonium sulfate. 5 ml of the Hib conjugate was applied to the HIC membrane at 1 ml/min and the membrane washed with the equilibration buffer until the absorbance at 280 nm returned to baseline. The conjugate was eluted from the membrane using 50 mM potassium phosphate buffer with 75% ethylene glycol as an additive. The membrane was cleaned with a 1 M NaOH (strip). Approximately 70% of the absorbance was found in the eluate peak.

Adsorption of Conjugate Using Sodium Chloride Instead of Ammonium Sulfate.

Figure 5:
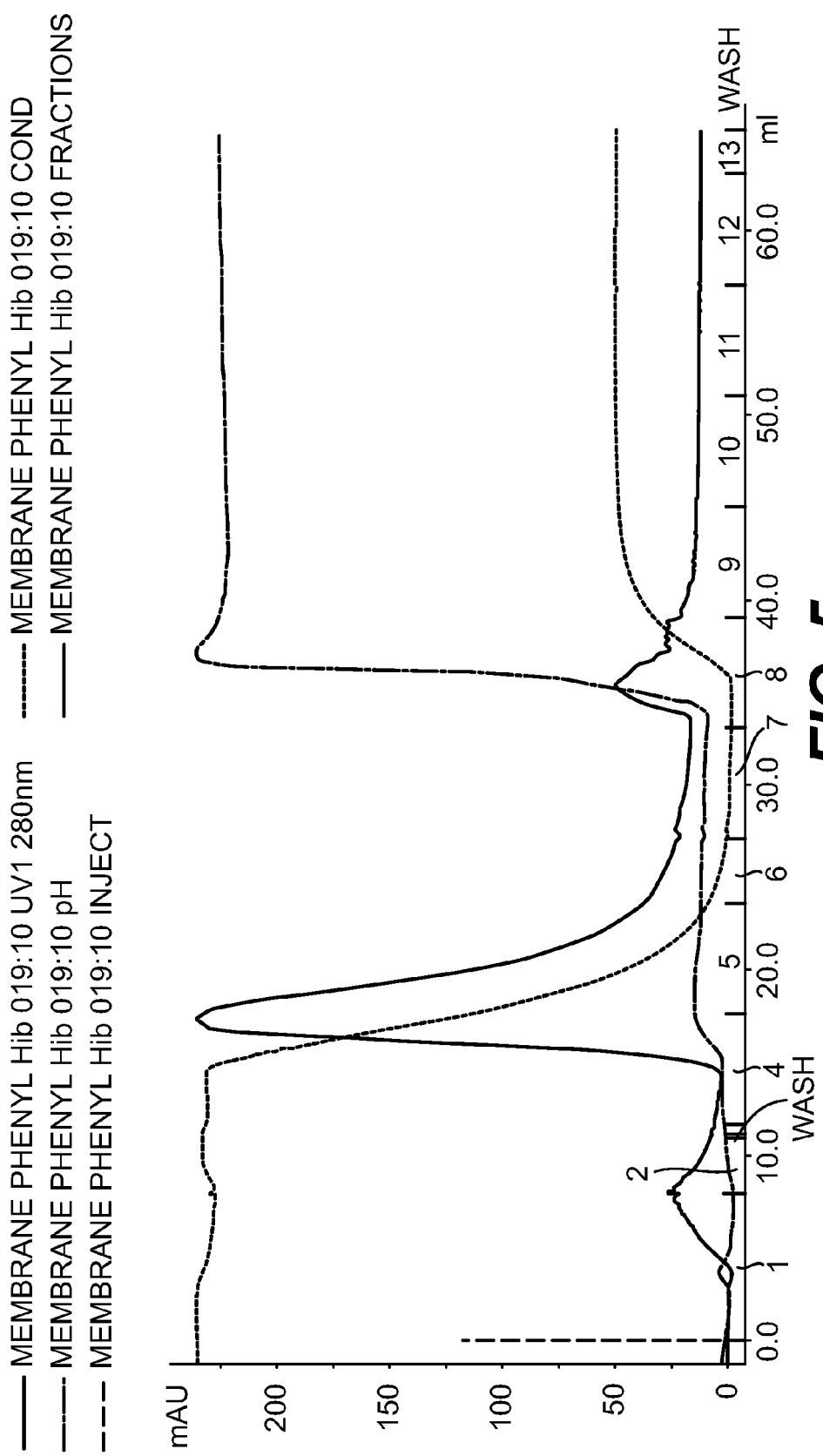
FIG. 5. Chromatogram of Hib conjugate bound to HIC membrane is a buffer containing 3 M sodium chloride.

Crude Hib conjugate was prepared in 25 mM Tris containing 3 M sodium chloride, pH 7.2 at an absorbance at 280 nm of about 1. 5 ml of the conjugate was applied to a Sartobind nano phenyl membrane at 1 ml/min. The membrane was washed with 2 column volumes of equilibration buffer and then eluted with 25 mM Tris, pH 7.2. It is seen in FIG. 5 that the conjugate was adsorbed to the membrane under these conditions and was eluted by decreasing the salt concentration. Thus, the invention is not limited to any particular salt for promoting hydrophobic binding.

Unconjugated PRP Polysaccharide Plus Tetanus Toxoid.

Illustration of the protein binds to the HIC membrane while the carbohydrate largely does not. A second aspect of the invention is that membrane chromatography may be used with conjugates, which are very large and interact poorly with ordinary porous chromatography media.

Figure 6A:
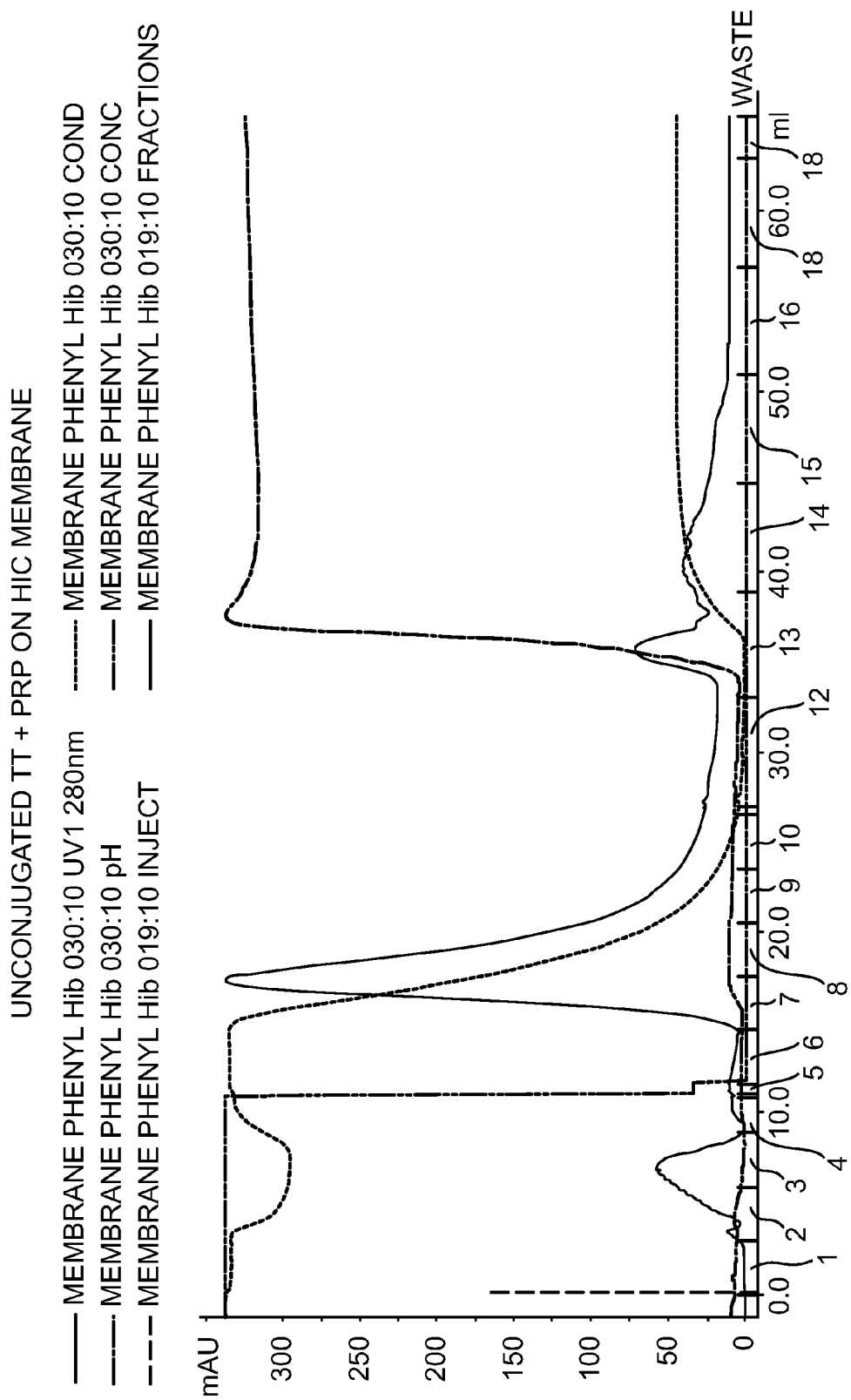
FIG. 6a. Chromatogram of a mixture of Hib PRP polysaccharide and Tetanus toxoid applied to an HIC membrane.
Figure 6B:
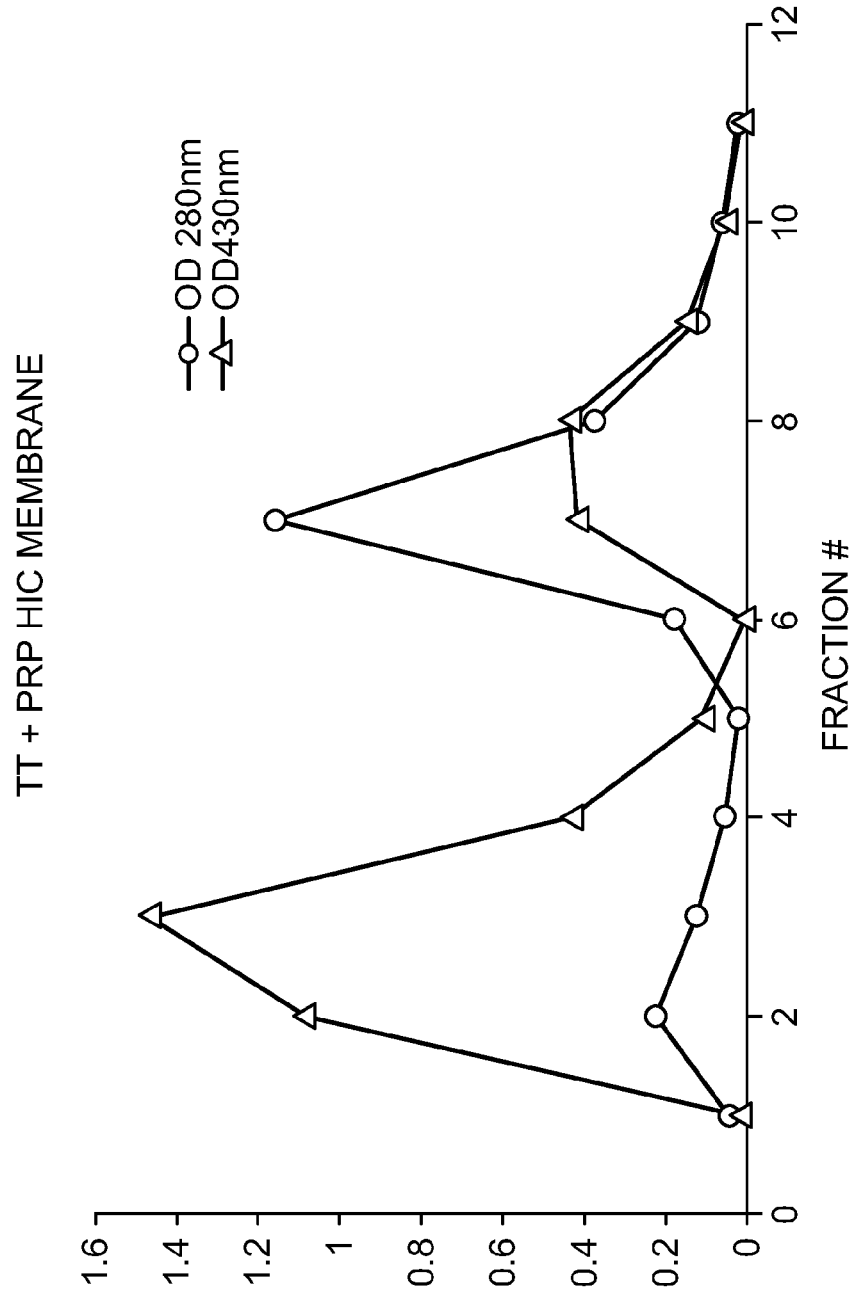
FIG. 6b. Assay of fractions from chromatogram of FIG. 6a. The protein and the carbohydrate monitored at an absorbance of 280 nm using the resorcinol/sulfuric acid assay (430 nm).

12 mg of tetanus toxoid plus 7 mg of PRP were made to 15 ml 3 M NaCl in 25 mM Tris, pH 7.2 and filtered through a 0.2 micron syringe device. 5 ml was applied at 1 ml/min to a 3 ml Sartorius nano HIC phenyl device, equilibrated with the same buffer. After washing with 2 column volumes of buffer, the column was eluted with a 2 column volume gradient to 25 mM Tris, pH 7.2. 3 ml fractions were collected (see FIG. 6a). The absorbance at 280 nm to monitor the protein and the carbohydrate was monitored using the resorcinol/sulfuric acid assay (see FIG. 6b). The flow through and elution peaks were pooled and again assayed, with the results shown in Table 1. Tetanus toxoid at approximately the same concentration as the eluant was also assayed.

TABLE 1

|  | Protein OD280 | Carbohydrate OD430 | OD280/430 |
| --- | --- | --- | --- |
| FT | 0.156 | 0.86 | 0.18 |
| Elute | 0.646 | 0.34 | 1.9 |
| TT | 0.55 | 0.04 | 13.8 |

Table 1 clearly indicates a marked enrichment of polysaccharide in the flow through pool and a marked enrichment of the protein component in the eluant pool. Tetanus toxoid does not contribute significantly to the absorbance at 430 nm.

Purification of tetanus toxoid conjugates of *Niesseria meningiditis* serotypes A, C, Y (TTMenA, TTMenC, TTMenY).

Men A, C and Y capsular polysaccharides of *Niesseria meningiditis* were functionalized with hexane diamine using a cyanating reagent and then linked to tetanus toxoid using thio-ether chemistry, as generally described in Lees et al. *Vaccine* 14:190, 1995. The product contained both free protein and polysaccharide along with the conjugated protein and polysaccharide. Each was dialyzed into saline and made up in 25 mM HEPES, pH 7.2+4 M NaCl. The conjugates, containing approximately equal amounts of protein and polysaccharide, were individually loaded onto the 3 ml Phenyl HIC membrane, equilibrated with the same buffer, at 0.5 ml/min, washed at 2 ml/min and eluted with 25 mM HEPES, pH 7.2 at 5 ml/min.

Figure 7:
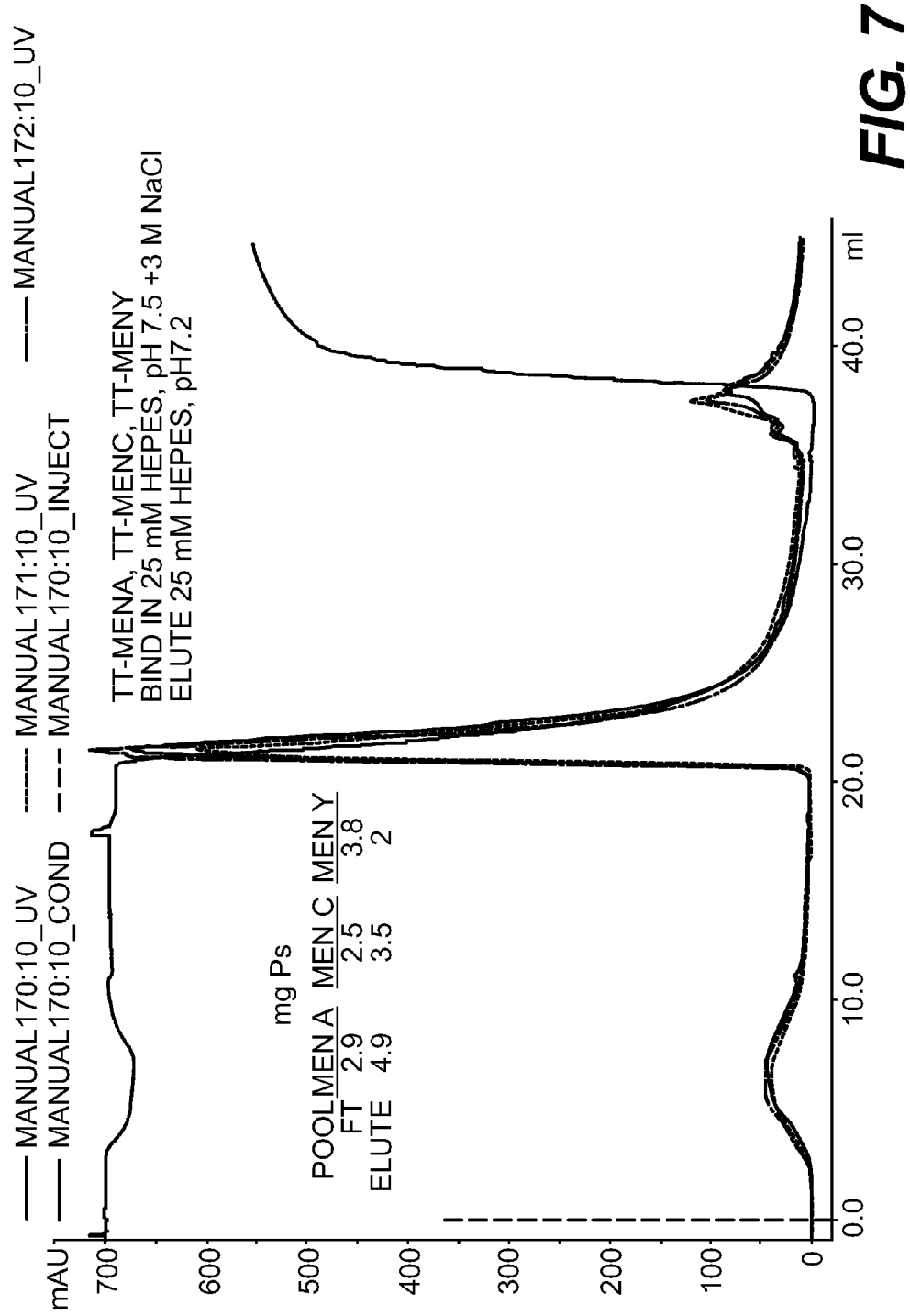
FIG. 7. An overlay of the chromatograms for three conjugates (TT-MenC, TT-MenY, TT-MenY) with monitoring at 280 nm.

FIG. 7 shows an overlay of the chromatograms for the 3 conjugates, with monitoring at 280 nm. The majority of the protein is in the elution pool and the table indicates that polysaccharide is in both the flow through and the elution pool. This example illustrates that the invention is broadly applicable as these *Neisseria* polysaccharides have a very different composition than PRP polysaccharide. Furthermore, these conjugates were prepared using a different chemistry than was used with the examples of the Hib conjugates.

CRM$_{197}$-Pneumococcal Ps Type 14 (Pn14).

CRM197 is linked to Pn14 using CDAP chemistry. The mixture containing both conjugated and unconjugated protein and polysaccharide is made 3 M sodium chloride in 25 mM Tris, pH 7.2. 3 mg (protein) of the mixture is applied to a Sartobind nano Phenyl membrane, equilibrated with the same buffer. After washing the membrane with equilibration buffer, the column is eluted with 25 mM Tris, pH 7.2. The eluant is found to be significantly enriched in the protein component, including the conjugate. This example illustrates the use of the invention for pneumococcal polysaccharides as well as the use of other proteins as the carrier protein.

*Salmonella* O-Specific Polysaccharide-TT. (OPS-TT).

A *Salmonella* OPS-TT conjugate mixture is prepared as described in Infection and Immunity 60:4679, 1992. The mixture contains both conjugated and free protein and polysaccharide. The mixture is made 3 M sodium chloride in 25 mM Tris, pH 7.2. 3 mg (protein) of the mixture is applied to a Sartobind nano Phenyl membrane, equilibrated with the same buffer. After washing the membrane with equilibration buffer, the column is eluted with 25 mM Tris, pH 7.2. The eluant is found to be significantly enriched in the protein component, including the conjugate, thus providing a conjugate with substantially reduced free carbohydrate.

Example TT-Detoxified Paratyphi A LPS Conjugate.

The conjugate is prepared as described in Infect Immun. 1996 July; 64(7):2709-15. The mixture contains both conjugated and free protein and polysaccharide. The mixture is made 3 M sodium chloride in 25 mM Tris, pH 7.2. 3 mg (protein) of the mixture is applied to a Sartobind nano Phenyl membrane, equilibrated with the same buffer. After washing the membrane with equilibration buffer, the column is eluted with 25 mM Tris, pH 7.2. The eluant is found to be significantly enriched in the protein component, including the conjugate, thus providing a conjugate with substantially reduced free carbohydrate.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A method for reducing the amount of free carbohydrate in a conjugate composition comprising:
   mixing the conjugate composition with a lyotropic salt;
   passing the mixture through a hydrophobic interaction membrane; and
   eluting the conjugate with an eluent.

2. The method of claim 1, wherein the carbohydrate comprises one or more of high molecular weight and low molecular weight polysaccharides, oligo saccharides, carbohydrate polymers, monomeric and polymeric sugars and combinations thereof.

3. The method of claim 1, which is independent of the chemistry used to create the conjugate and independent of type of carrier protein used.

4. The method of claim 1, wherein the conjugate is eluted with an eluent containing a reduced concentration of the lyotropic salt.

5. The method of claim 4, wherein the lyotropic salt is ammonium sulfate or NaCl.

6. The method of claim 1, wherein the eluent further includes an additive.

7. The method of claim 6, wherein the additive is an organic solvent, a detergent, or both.

8. The method of claim 6, wherein the additive is ethylene glycol.

9. The method of claim 1, wherein eluting is performed as a step or continuous gradient.

10. The method of claim 1, wherein greater than 50% of free carbohydrate is removed from the conjugate composition.

11. The method of claim 1, wherein greater than 90% of free carbohydrate is removed from the conjugate composition.

12. A method for reducing the amount of free carbohydrate in a conjugate composition comprising:
   mixing the conjugate composition with a lyotropic salt;
   passing the mixture through a monolith matrix or column; and
   eluting the conjugate with an eluent.

13. The method of claim 12, wherein the monolith matrix or column is a phenyl monolith.

14. The method of claim 12, wherein the eluent further includes an additive.

15. The method of claim 14, wherein the additive is an organic solvent, a detergent, or both.

16. The method of claim 14, wherein the additive is ethylene glycol.

17. The method of claim 12, wherein the conjugate is a vaccine.

18. The method of claim 12, wherein greater than 50% of free carbohydrate is removed from the conjugate composition.

19. The method of claim 12, wherein greater than 90% of free carbohydrate is removed from the conjugate composition.

* * * * *